United States Patent [19]
Lin et al.

[11] Patent Number: 5,177,017
[45] Date of Patent: Jan. 5, 1993

[54] **MOLECULAR CLONING OF THE GENES RESPONSIBLE FOR COLLAGENASE PRODUCTION FROM *CLOSTRIDIUM HISTOLYTICUM***

[75] Inventors: Hun-Chi Lin; Shau-Ping Lei, both of Los Angeles, Calif.

[73] Assignee: Trigen, Inc., Santa Monica, Calif.

[21] Appl. No.: 498,919

[22] Filed: Mar. 22, 1990

[51] Int. Cl.$^5$ .................. C12N 15/57; C12N 15/70; C12N 15/31
[52] U.S. Cl. ................. 435/252.33; 435/220; 435/320.1; 935/14; 935/29; 935/73; 536/23.7
[58] Field of Search ................. 435/69.1-69.9, 435/320.1, 220, 252.33; 536/27

[56] References Cited

U.S. PATENT DOCUMENTS 3,705,083 12/1972 Chiulli et al. ............... 435/70.2

OTHER PUBLICATIONS

Biochemistry, vol. 23, No. 22, issued Oct. 23, 1984, Sugasawara, et al., "Purification and Characterization of Three Forms of Collagenase From *Clostridium histolyticum*", pp. 5175-5181.

Proceedings of the National Academy of Sciences USA, vol. 82, May 1985, Young, et al., "Dissection of *Mycobacterium tuberculosis* Antigens Using Recombinant DNA", pp. 2583-2587.

Clinical Orthopedics and Related Research, No. 215, Feb. 1987, K. H. Chu, "Collagenase Chemonucleolysis Via Epidural Injection: A Review of 252 Cases", pp. 99-104.

Biochemistry, vol. 27, No. 19, Sep. 20, 1988, Angelton, et al., "Preparation and Reconstitution With Divalent Metal Ions of Class I and Class II *Clostridium histolyticum* Apocollagenases", pp. 7406-7412.

Biochemistry, vol. 27, No. 19, Sep. 20, 1988, Angleton et al., "Preparation by Direct Metal Exchange and Kinetic Study of Active Site Metal Substituted Class I and Class II *Clostridium histolyticum* Collagenases", pp. 7413-7418.

M. D. Bond & H. E. Van Wart, "Purification and Separation of Individual Collagenases of *Clostridium histolyticum* Using Red Dye Ligand Chromatography," Biochemistry 23, 3077-3085 (1984).

M. D. Bond & H. E. Van Wart, "Characterization of the Individual Collagenases from *Clostridium histolyticum*," Biochemistry 23, 3085-3091 (1984).

M. D. Bond & H. E. Van Wart, "Relationship Between the Individual Collagenases of *Clostridium histolyticum*: Evidence for Evolution by Gene Duplication," Biochemistry 23, 3092-3099 (1984).

M. F. French, K. A. Mookhtiar & H. E. Van Wart, "Limited Proteolysis of Type I Collagen and Hyperreactive Sites by Class I and II *Clostridium histolyticum* Collagenases: Complementary Digestion Patterns," Biochemistry 26, 681-687 (1987).

(List continued on next page.)

Primary Examiner—Robert A. Wax
Assistant Examiner—William W. Moore
Attorney, Agent, or Firm—Poms, Smith, Lande & Rose

[57] ABSTRACT

Genetically engineered *E. coli* carry vectors containing inserts that code for *Clostridium histolyticum* collagenase. These inserts code for: (a) a form of collagenase having a molecular weight of about 68,000 daltons in the essential absence of larger forms of collagenase; (b) the 68 kd form of collagenase and a fusion polypeptide consisting of the collagenase protein fused to at least a portion of the β-galactosidase protein of *E. coli*; or (3) the 68 kd form of collagenase and polypeptides of molecular weight of from above about 68,000 daltons to about 100,000 daltons and having the enzymatic activity of *C. histolyticum* collagenase as indicated by digestion of $^3$H-acetylated collagen and by specific inhibition by 1,10-phenanthroline plus EDTA. The collagenase genes in the transformed *E. coli* are expressed efficiently in the transformed cells to yield enzymatically active and immunologically cross-reactive collagenase. In particular, the 68 kd form of collagenase is resistant to autocatalytic degradation and is stable to long-term storage. Genetically engineered collagenase, especially the 68 kd form that is resistant to autocatalytic degradation, can be used for isolation of pancreatic islets, for the isolation of dispersed tumor cells, or for treatment of "slipped disc."

23 Claims, 8 Drawing Sheets

OTHER PUBLICATIONS

S. K. Mallya, K. A. Mookhtiar & H. E. Van Wart, "Accurate, Quantitative Assays for the Hydrolysis of Soluble Type I, II and III $^3$H-Acetylated Collagens by Bacterial and Tissue Collagenases," *Anal. Biochem.* 158, 334–345 (1986).

K. A. Mooktiar, D. R. Steinbrink and H. E. Van Wart, "Mode of Hydrolysis of Collagen-like Peptides by Class I and Class II *Clostridium histolyticum* Collagenases: Evidence for Both Endopeptidase and Tripeptidylcarboxypeptidase Activities," *Biochemistry* 24, 6527–6533 (1985).

K. A. Mookhtiar, S. K. Mallya and H. E. Van Wart, "Properties of Radiolabeled Type I, II, and III Collagens Related to Their Use as Substrates in Collagenase Assays," *Anal. Biochem.* 158, 322–333 (1986).

H. E. Van Wart & D. R. Steinbrink, "Complementary Substrate Specificities of Class I and Class II Collagenases from *Clostridium histolyticum*," *Biochemistry* 24, 6520–6526 (1985).

E. Wunsch & H.-G. Heidrich, "Zur Quantitativen Bestimmung der Kollagenase," *Hoppe-Seyler's Zeit. Physiol. Chem.* 333, 149–151 (1963).

E. Amann, J. Brosius & M. Ptashne, "Vectors Bearing a Hybrid trp-lac Promoter Useful for Regulated Expression of Cloned Genes in *Escherichia coli*," *Gene* 25, 167–178 (1983).

W. N. Burnette, "'Western Blotting': Electrophoretic Transfer of Proteins from Sodium Dodecyl Sulfate-polyacrylamide Gels to Unmodified Nitrocellulose and Radiographic Detection with Antibody and Radioiodinated Protein A," *Anal. Biochem.* 112, 195–203 (1981).

D. Hanahan, "Studies on Transformation of *Escherichia coli* with Plasmids," *J. Mol. Biol.* 166, 557–580 (1983).

T. V. Huynh, R. A. Young & R. W. Davis, "Constructing and Screening cDNA Libraries in λgt10 and λgt11," In *DNA Cloning Techniques: A Practical Approach* (ed. D. Glover), (IRL Press, Eynsham, 1975, vol. I, pp. 49–79.

M. Russel, S. Kidd & M. R. Kelley, "An Improved Filamentous Helper Phage for Generating Single-stranded Plasmid DNA," *Gene* 45, 333–338 (1986).

J. Shine & L. Dalgarno, "Determinant of Cistron Specificity in Bacterial Ribosomes," *Nature* 254, 34–38 (1975).

J. M. Short, J. M. Fernandez, J. A. Sorge & W. D. Huse, "λZAP: A Bacteriophage λ Expression Vector with in Vivo Excision Properties," *Nucl. Acid. Res.* 16, 7583–7600 (1988).

R. A. Young, B. R. Bloom, C. M. Grosskinsky, J. Ivanyi, D. Thomas & R. W. Davis, "Dissection of *Mycobacterium tuberculosis* Antigens Using Recombinant DNA," *Proc. Natl. Acad. Sci. USA* 82, 2583, (1985).

R. A. Young & R. W. Davis, "Efficient Isolation of Genes by Using Antibody Probes," *Proc. Natl. Acad. Sci. USA* 80, 1194–1198 (1983).

R. A. Young & R. W. Davis, "Yeast RNA Polymerase II Genes: Isolation with Antibody Probes," *Science* 222, 778–782 (1983).

R. A. Young, V. Mehra, D. Sweetser, T. Buchanan, J. Clark-Curtiss, R. W. Davis & B. R. Bloom, "Genes for the Major Protein Antigens of the Leprosy Parasite *Mycobacterium leprae*," *Nature* 317, 450–452 (1985).

D. W. R. Gray & P. J. Morris, "Prospects for Pancreatic Islet Transplantation," *World J. Surg.* 10, 410–421 (1986).

J. S. Najarian, D. E. R. Sutherland, A. J. Matas, M. W. Steffes, R. L. Simmons & F. C. Goetz, "Human Islet Transplantation: A Preliminary Report," *Transplantation Proc.* 9, 233–236 (1977).

D. W. Scharp, "Isolation and Transplantation of Islet Tissue," *World J. Surg.* 8, 143–151 (1984).

D. E. R. Sutherland, A. J. Matas, F. C. Goetz & J. S. Najarian, "Transplantation of Dispersed Pancreatic Islet Tissue in Humans: Autografts and Allografts," *Diabetes* 29, Suppl. 1, 31–44 (1980).

B. J. Sussman, J. W. Bromley & J. C. Gomez, "Injection of Collagenase in the Treatment of Herniated Lumbar Disk: Initial Clinical Report," *J. Am. Med. Assn.* 245, 730–732 (1981).

R. G. Fisher, J. W. Bromley, G. L. Becker, M. Brown & V. Mooney, "Surgical Experience Following Intervertebral Discolysis with Collagenase," *J. Neurosurg.* 64, 613–616 (1986).

K. H. Chu, "Collagenase Chemonucleolysis via Epidural Injection: A Review of 252 Cases," *Clin. Orthopedics & Related Res.* No. 215, 99–104 (Feb. 1987).

Jaye, M., et al., 1983, Nucleic Acids Research, 11(8): 2325–2335.

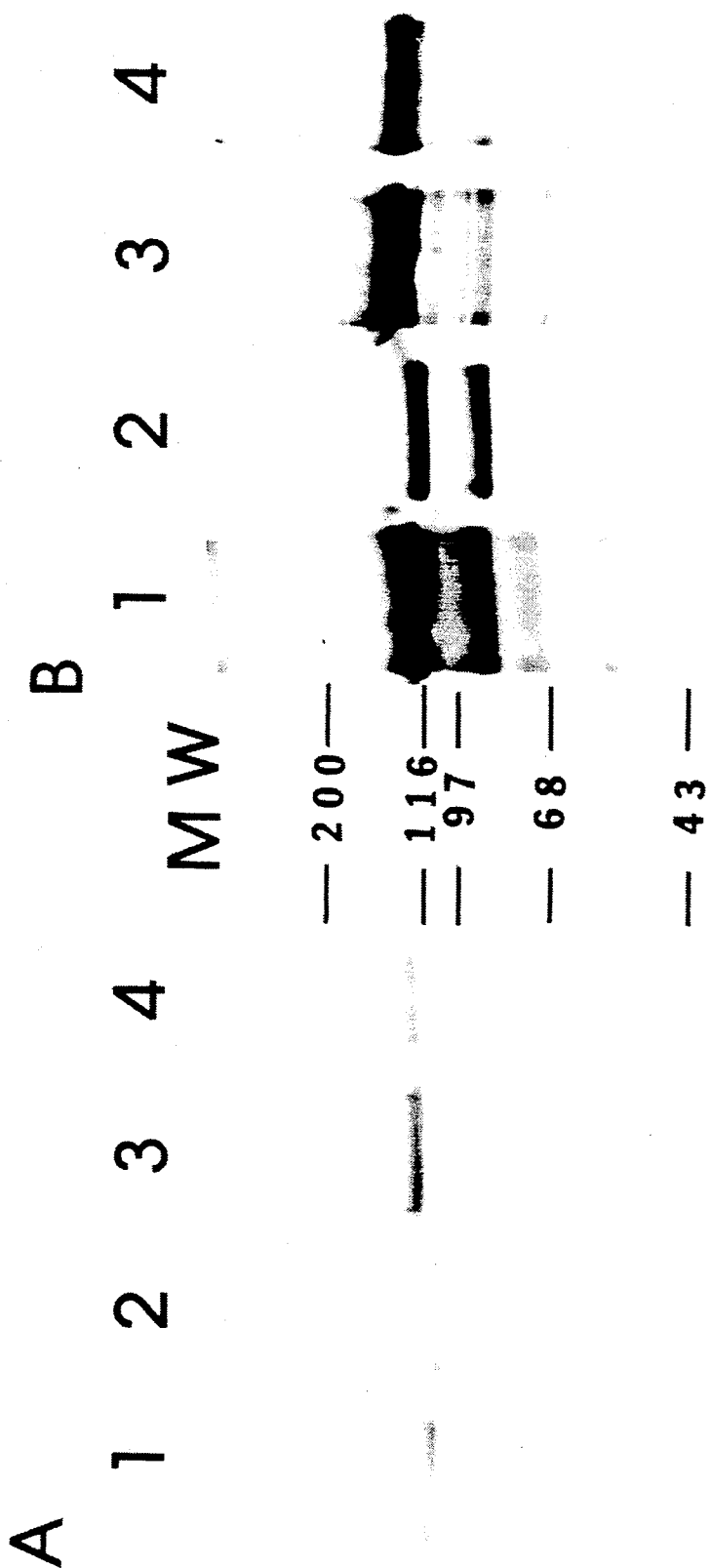

MOLECULAR CLONING OF THE GENES RESPONSIBLE FOR COLLAGENASE PRODUCTION FROM *CLOSTRIDIUM HISTOLYTICUM*

The research reported in this application in support of the invention herein received assistance from a grant provided by the Department of Health & Human Services, Public Health Service, National Institute of Diabetes, Digestive and Kidney Disease, Grant No. N43-DK-8-2239.

BACKGROUND

This invention relates to the isolation and cloning of genetic information coding for *Clostridium histolyticum* collagenase and the expression of the genetic information in a suitable host. In particular, this invention is directed to the isolation and cloning of genetic information coding for a single form of *Clostridium histolyticum* collagenase useful for the reproducible isolation of pancreatic islets from pancreatic tissue.

Patients with Type I diabetes are insulin-dependent because they are unable to produce insulin from the endocrine portion of the pancreas. Whole-pancreas transplantation has been used in an effort to improve the quality of life of diabetic patients and to prevent the long-term complications of the disease such as blindness, peripheral neuropathy, and coronary artery disease.

For insulin-dependent patients, whole-pancreas transplantation has the disadvantage that transplantation of only the endocrine component of the pancreas, the pancreatic islets, is required to correct the insulin deficiency. The remaining exocrine portion of the gland complicates and frequently hampers successful transplantation. Management of the exocrine secretions of the pancreas poses a major technical problem in the treatment of Type I diabetes by whole organ transplantation.

It would, therefore, be desirable to treat diabetes by transplantation of the pancreatic islets instead of the whole pancreas. For that reason, much effort has gone into isolating the islets from the human pancreas for clinical islet transplantation. These efforts have been reviewed in D. W. R. Gray & P. J. Morris, "Prospects for Pancreatic Islet Transplantation," *World J. Surg.* 10, 410–421 (1986) and D. W. Scharp, "Isolation and Transplantation of Islet Tissue," *World J. Surg.* 8, 143–151 (1984).

Among the enzymes most suitable for cell isolation is collagenase. Collagenase is a protease specific for the fibrous protein collagen of connective tissue. Collagenase digestion of pancreases for islet cell isolation has been used with some success with pancreases of small animals, but with considerably less success in the more fibrous human pancreas. The clinical results of islet cell transplantation have been poor, as detailed in J. S. Najarian, D. E. Sutherland, A. J. Matas, M. W. Steffes, R. L. Simmons, & F. C. Goetz, "Human Islet Transplantation: A Preliminary Report," *Transplant Proc.* 9, 233–235 (1977), and D. E. Sutherland, A. J. Matas, F. C. Goetz, & J. S. Najarian, "Transplantation of Dispersed Pancreatic Islet Tissue in Humans: Autografts and Allografts," *Diabetes [Supp.]*29, 31–35 (1980). The islet cells obtained have relatively poor viability and are contaminated with exocrine cells.

One of the technical difficulties with human islet isolation stems from inherent lot-to-lot variation in commercially available preparations of collagenase. The underlying reason for this lot-to-lot variation is not understood. Each of the several types of collagenase commercially available requires extensive screening and testing to ensure its efficiency.

Another problem associated with the use of collagenase in human islet cell isolation is that commercial collagenase preparations from *C. histolyticum* contain highly active non-collagenase proteases that may contribute more proteolytic activity than does the collagenase itself. This further complicates the problem of obtaining a reproducible collagenase preparation for use in islet cell isolation.

The use of Clostridium collagenase for the isolation of pancreatic islets is still further complicated by the existence of multiple forms of collagenase produced by Clostridium. As many as six separate forms of collagenase can be present: α-collagenase, β-collagenase, γ-collagenase, δ-collagenase, ζ-collagenase, and ξ-collagenase. Furthermore, some of these forms are present in subspecies. All of these multiple forms of collagenase are highly active against collagen and devoid of other proteolytic activities. They have molecular weights ranging from 68,000 daltons to 125,000 daltons as determined by sodium dodecyl sulfate-polyacrylamide gel electrophoresis. The problem of obtaining preparations of collagenase for reproducible islet cell isolation is further complicated by the fact that many of these forms of collagenase are subject to rapid autocatalytic proteolysis and are degraded to smaller molecules.

The existence of multiple forms of collagenase, contaminating non-collagenase proteases, and rapid autocatalytic proteolytic degradation all contribute to lot-to-lot variation in the activity of commercial Clostridium collagenase. It is not known what factors, such as the strain of Clostridium used, growth medium, growth conditions, or time of harvest, are responsible for this variability. The existence of this variability complicates efforts to use Clostridium collagenase for the isolation of pancreatic islets from human pancreatic tissue because it creates a lack of reproducibility in the isolation of the islets.

Accordingly, there is a need for a method to isolate human islets reproducibly so that the effects of lot-to-lot variations of collagenase enzyme preparations are minimized. In particular, there is a need for preparations of collagenase that are stable and are not subject to autocatalytic degradation for use in islet cell isolation.

SUMMARY

We have developed a procedure by which the collagenase genes of Clostridium can be cloned and individually expressed in *E. coli*. This procedure allows the production of unlimited quantities of a single form of enzymatically active and immunologically reactive collagenase by genetically engineered *E. coli*. This collagenase, unlike previously available *C. histolyticum* collagenases, has the highly desirable property that it is sufficiently resistant to autocatalytic degradation to be stable for 2 days at 25° C. Preparations of this collagenase can be used for digestion of tissue and for cell isolation, including isolation of pancreatic islets.

In our study of the cloned Clostridium DNA we have found that a single segment of DNA can code for both a 68 kd form of collagenase and a large form of collagenase whose exact size is difficult to determine because of its high molecular weight, but which includes polypeptides from about 70,000 daltons in molecular weight to about 100,000 daltons, and possibly larger polypeptides. These two forms of collagenase are expressed colinearly (i.e, the same sequence of DNA is read in the same reading frame to produce mRNA for both proteins); both react with the same anti-collagenase antibody. Production of the large form of collagenase requires the functioning of an external promoter supplied by a plasmid into which the segment is incorporated, while the production of the 68 kd form of collagenase does not require an external promoter. Transcription of the portion of the DNA coding for the 68 kd form of collagenase is under the control of a promoter located within the portion of the DNA coding for the large form of the collagenase. This leads to the conclusion that a single portion of the cloned Clostridium DNA can serve as both a promoter and part of a structural gene. The existence of such a phenomenon was unknown and unsuspected in Clostridium.

Aspects of the invention include: (1) substantially purified collagenase produced by genetically engineered E. coli containing Clostridium DNA inserts; (2) inserts of Clostridium DNA that are capable of coding for either the 68 kd form of Clostridium collagenase or both the 68 kd and large forms of collagenase; (3) vectors containing the inserts of Clostridium DNA that are suitable for transforming E. coli; (4) E. coli transformed by the vectors and producing recoverable quantities of enzymatically active collagenase; and (5) methods of using substantially purified genetically engineered collagenase for tissue digestion and cell isolation.

1. Purified Collagenase Produced by Genetically Engineered E. coli

A significant aspect of the invention is a substantially purified preparation of C. histolyticum collagenase having a molecular weight of about 68,000 daltons and sufficiently resistant to autocatalytic degradation that it is substantially stable on storage for about 2 days at about 25° C. This preparation is purified from E. coli stably transformed with a vector containing Clostridium DNA.

2. Inserts of Clostridium DNA Coding for Collagenase

Another important aspect of the invention is the provision of inserts of Clostridium DNA coding for either the 68 kd form of collagenase, or both the large form and the 68 kd form of collagenase. The inserts fall into two categories: (1) inserts in which the collagenase gene is not fused to another gene, such as the β-galactosidase gene of E. coli; and (2) inserts in which the collagenase gene is fused with the E. coli β-galactosidase gene. The second class of inserts produces collagenase as a fusion protein in which collagenase is fused with at least a portion of the E. coli β-galactosidase protein.

a. Non-fusion Inserts

There are two types of non-fusion inserts: (1) inserts coding solely for the 68 kd form of collagenase and (2) inserts coding for both the 68 kd form and the large form of collagenase.

The first type is a recombinant DNA sequence comprising DNA derived from Clostridium histolyticum coding solely for a polypeptide having the enzymatic activity of C. histolyticum collagenase as indicated by digestion of $^3$H-acetylated collagen and by specific inhibition by 1,10-phenanthroline plus EDTA, the polypeptide having a molecular weight of about 68,000 daltons. Typically, this DNA insert is capable of being translated to yield a polypeptide of about 68,000 daltons molecular weight and having collagenase activity, the polypeptide being distinguishable from the collagenase of C. histolyticum produced in vivo by the essential absence of forms of C. histolyticum collagenase having molecular weights of above about 70,000 daltons in the products of translation. The DNA insert is also typically capable of being transcribed to yield mRNA capable of being transcribed to yield a peptide displaying the antigenicity of C. histolyticum collagenase.

To be activated for transcription, the insert must be operatively linked to a promoter. The promoter can be within the inserted Clostridium DNA such that the DNA can be transcribed under control of the promoter to yield mRNA capable of being translated to yield the polypeptide of about 68,000 daltons without the functioning of a promoter external to the DNA derived from C. histolyticum. Alternatively, the inserted DNA sequence can be fused contiguously to a transcription-effecting DNA sequence selected from the group consisting of Escherichia coli lac promoter, E. coli trp promoter bacteriophage λ P$_L$ promoter, and tac promoter such that the transcription-effecting sequence can effect transcription of the DNA derived from C. histolyticum.

The second type of non-fusion insert can code for both the 68 kd form and the large form of collagenase and is capable of expressing both forms. Typically, such an insert is a recombinant DNA sequence comprising: (1) a Clostridium histolyticum structural gene encoding C. histolyticum collagenase and capable of being transcribed to yield mRNA capable of being translated to yield polypeptides of molecular weight of from about 70,000 daltons to about 100,000 daltons and cross-reacting immunochemically with antibody to at least one class of C. histolyticum collagenase; and (2) an internal promoter located within the structural gene of (1) and operatively linked to a Clostridium DNA sequence comprising a portion of the structural gene of (1) and capable of being transcribed to yield mRNA capable of being translated to yield a polypeptide of about 68,000 daltons molecular weight. The polypeptide is distinguishable from the collagenase of C. histolyticum produced in vivo by the essential absence of forms of C. histolyticum collagenase having molecular weights of above about 70,000 daltons in the products of translation. The internal promoter is positioned such that the DNA sequence of (2) can be translated independently of the structural gene of (1). Such a DNA sequence is typically fused contiguously to a transcription-effecting DNA sequence selected from the group consisting of E. coli lac promoter, E. coli trp promoter, bacteriophage λ P$_L$ promoter, and tac promoter such that the transcription-effecting sequence can effect transcription of the structural gene of (1). In such an arrangement, both the entire C. histolyticum structural gene and the DNA sequence coding for the 68 kd collagenase polypeptide are capable of being alternatively and colinearly expressed to produce C. histolyticum collagenase having molecular weights ranging from about 68,000 daltons to about 100,000 daltons. The internal promoter activating transcription of the 68 kd polypeptide is capable of coding for and being read as an internal amino acid sequence of the structural gene of (1). This means that the same portion of DNA sequence is used twice: once as a promoter and once as a structural gene.

b. Fusion Inserts

Fusion inserts are inserts in which the inserted Clostridium DNA, including the gene for collagenase, is fused contiguously in an open reading frame to at least a portion of the structural gene for *E. coli* β-galactosidase. The portion of the structural gene for β-galactosidase is operatively linked to a lac promoter such that:

(1) the DNA derived from Clostridium can be transcribed under control of the promoter located within the Clostridium DNA to yield mRNA capable of being translated to yield the polypeptide of about 68,000 daltons without the functioning of a promoter external to the DNA derived from *C. histolyticum*; and (2) the Clostridium DNA fused to the DNA sequence comprising at least a portion of the structural gene for *E. coli* β-galactosidase can be transcribed under control of the lac promoter to yield mRNA capable of being translated to yield a fusion polypeptide of molecular weight greater than 70,000 daltons displaying the antigenicity of *C. histolyticum* collagenase and containing at least a portion of the amino acid sequence of *E. coli* β-galactosidase. Therefore, such fusion inserts produce at least two polypeptides with the antigenicity of *C. histolyticum* collagenase.

3. Vectors for Transforming *Escherichia coli*

Any of the DNA sequences that encode Clostridium collagenase can be incorporated into a vector comprising the DNA sequence incorporated into a plasmid capable of stably transforming *E. coli* host cells. Such a plasmid is selected from the group of plasmids consisting of those with both a drug resistance marker and a replication origin. Typically, the plasmid is generated in vivo by rescue of λzap DNA containing the inserted Clostridium DNA by M13 helper phage.

4. Transformed *E. coli*

Another aspect of the invention is *E. coli* transformed with any of the vectors described above that incorporate the Clostridium DNA inserts.

5. Methods for Use of Collagenase Produced by Genetically Engineered *E. coli*

Yet another aspect of the invention is methods for use of substantially purified collagenase produced by genetically engineered *E. coli*. These methods are suitable for such purposes as digesting connective tissue and releasing embedded cells, isolating dispersed pancreatic islets from pancreatic tissue, and dissociating tumors for isolation of dispersed tumor cells. The methods comprise two steps:

(1) incubating the tissue to be dispersed in a buffered solution containing the substantially purified genetically engineered collagenase with shaking at about 25°–37° C. to release and disperse the embedded cells; and (2) separating the dispersed cells from tissue debris. The step of separating the dispersed cells from tissue debris is typically performed by density gradient centrifugation.

The genetically engineered *C. histolyticum* collagenase can also be used in a method for intradiscal treatment of herniation of nucleus pulposus ("slipped disc"). This method comprises the steps of:

(1) preparing a sterile buffered solution containing substantially purified genetically engineered collagenase; and (2) injecting the sterile buffered solution containing the substantially purified genetically engineered collagenase into the nucleus pulposus.

BRIEF DESCRIPTION OF THE DRAWINGS

These and other features, aspects, and advantages of the present invention will become better understood with reference to the following description, appended claims, and the accompanying drawings where:

FIG. 1a and 1b show the results of an SDS-polyacrylamide electropherogram of purified collagenases, FIG. 1a is a Western-blotted preparation and FIG. 1b is a Coomassie-blue stained preparation;

FIG. 2a is a Western-blotted preparation and FIG. 2b is a Coomassie-blue stained preparation;

FIG. 6 shows the results of Western immunoblotting of lysates of *E. coli* carrying plasmid P42 and its subclones; and FIG. 7A schematically depicts the in vivo mutagenesis process used to add four nucleotides to the insert of plasmid pRS21 to disrupt the reading frame and FIG. 7B shows the results of Western immunoblotting of lysates of *E. coli* cells carrying pRS21 and the mutated plasmid, pRS21-8.

DESCRIPTION

Figures 2A, 2B:
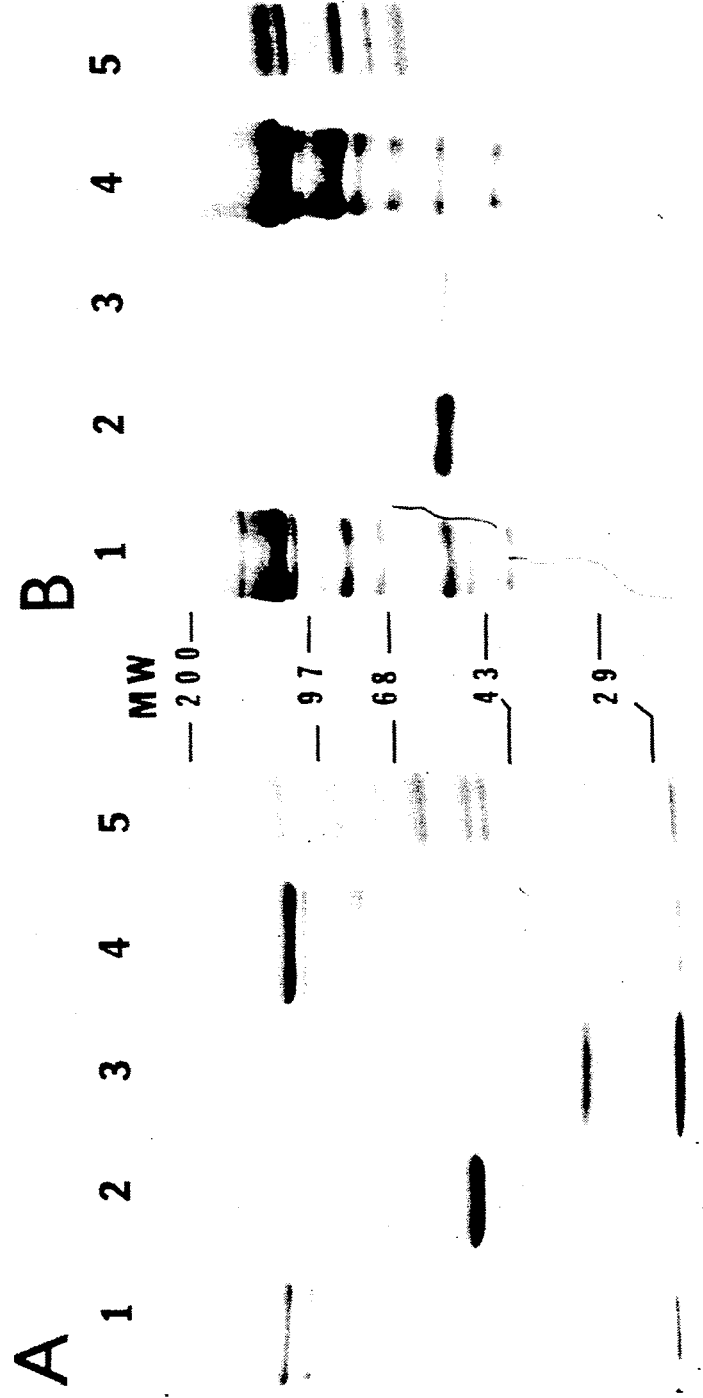
FIGS. 2a and 2b show the results of an SDS-polyacrylamide electropherogram of purified collagenases after two months of storage at −80° C.

I. Clostridium Collagenase Produced By Genetic Engineering

We have cloned a gene for *Clostridium histolyticum* collagenase into *E. coli*. The cloned gene is capable of expression as a polypeptide product in *E. coli*. The product expressed in *E. coli* is detectable both in the form of protein immunoreactive with anticollagenase antibody and in the form of assayable collagenase activity.

It was found that the same sequence of DNA could be translated colinearly to yield several types of collagenase. From one DNA insert of about 4 kilobases (kb), designated P42, are produced at least six different polypeptides ranging in molecular weight from about 68 kilodaltons (kd) to about 100 kd. All of these polypeptides react with anticollagenase antibody. It is likely that all of these polypeptides, except for the 68 kd polypeptide, are products of limited autolysis of at least one original polypeptide that is 100 kd in size or larger. The original polypeptide or polypeptides may also be present. These larger polypeptide or polypeptides are referred to collectively as the "large form" of collagenase. As seen in these experiments, the large form of collagenase includes polypeptides of molecular weight of from about 70,000 daltons to about 100,000 daltons. These polypeptides cross-react immunologically with the same antibody to which the 68 kd form of collagenase also reacts, and are believed to have collagenase activity. As is described below, the 68 kd protein is under the independent control of an internal promoter and can be transcribed and translated separately even under conditions in which the large form is not transcribed or translated.

The 68 kd form of collagenase is enzymatically active and has the enzymatic properties of Clostridium collagenase. It digests collagen efficiently as determined by the digestion of $^3$H-acetylated collagen and is inhibited by a specific inhibitor of Clostridium collagenase, 1,10- phenanthroline. The large form of collagenase produced in genetically engineered *E. coli* may also be enzymatically active.

The 68 kd form of collagenase produced in genetically engineered *E. coli* is relatively resistant to autocatalytic degradation. This form of collagenase is substantially stable for about 2 days at about 25° C. It is therefore particularly useful for digestion of pancreatic tissue for the isolation of islets, as well as for other applications employing collagenase.

II. Insertes Producing Collagenase

It has been found that several classes of inserts containing Clostridium DNA are capable of coding for and expressing collagenase in *E. coli*. These inserts either code for: (1) the autocatalytic-degradation-resistant 68 kd form of collagenase alone or (2) for the 68 kd form accompanied by the large form of collagenase.

Typically, the DNA segment of the insert is fused contiguously to a transcription-effecting DNA sequence that controls and activates transcription from the Clostridium DNA segment. Generally, such a transcription-effecting DNA sequence is not itself derived from Clostridium and includes a promoter derived from a procaryote or virus infecting a procaryote and capable of activating transcription under regulation in *E. coli*. Such promoters include, but are not limited to, the *E. coli* lac promoter, the *E. coli* trp promoter, the bacteriophage λ $P_L$ promoter, the bacteriophage T7 promoter, and the tac promoter, a hybrid trp-lac promoter that is regulated by lac repressor (E. Amann, E. J. Brosius & M. Ptashne, "Vectors Bearing a Hybrid trp-lac Promoter Useful for Regulated Expression of Cloned Genes in *Escherichia coli*," Gene 25, 167 (1983)). The use of an external transcription-effecting sequence is not required in all cases, particularly when only the 68 kd form of collagenase is produced in larger quantities. This is because that form of collagenase can be transcribed as a result of the action of an internal promoter lying within the first part of the Clostridium collagenase DNA insert itself. This promoter can control the transcription of that portion of the insert downstream from it to yield mRNA capable of being translated to yield the 68 kd form of collagenase, without the functioning of any promoter external to the DNA derived from *C. histolyticum*. Because the Clostridium promoter is actually located within the structural gene for the large form of collagenase, it cannot serve to activate transcription of that form.

Optimally, a ribosome-binding site is provided between the promoter and the beginning of the Clostridium DNA. This is a sequence known as the Shine-Dalgarno sequence and complementary to the 3'-terminus of *E. coli* 16S ribosomal RNA (rRNA). It is typically located 3-11 nucleotides upstream of the ATG initiation codon of the DNA. (J. Shine & L. Dalgarno, "Determinant of Cistron Specificity in Bacterial Ribosomes," Nature 254, 34 (1975)).

The DNA inserts capable of expressing collagenase fall into two categories: (1) inserts in which the collagenase gene is not fused to another gene; and (2) inserts in which the collagenase gene is fused with the *E. coli* β-galactosidase gene. The second class of inserts produces collagenase as a fusion protein with at least a portion of the *E. coli* β-galactosidase protein, as well as producing the 68 kd form of collagenase.

A. Non-fusion Inserts

The DNA inserts that do not express collagenase as a fusion protein fall into several categories:

(1) Inserts coding only for the 68 kd form of collagenase and expressing only that form of the protein; and (2) Inserts having the coding capacity for both the 68 kd form and the large form of the collagenase protein.

1. Inserts Coding Only For the 68 kd Form of Collagenase and Expressing That Form A first class of Clostridium DNA inserts, exemplified by the 1.7 kb Clostridium DNA insert of the plasmid pRS21 (Example 12), codes only for the 68 kd form of collagenase and expresses that form of collagenase efficiently. This class of inserts produces a form of collagenase distinguishable from the collagenase produced by *C. histolyticum* in vivo by the essential absence of forms of collagenase having molecular weights of above about 70,000 daltons in the products of translation. Of course, the size of that insert precludes it from coding for the large form of collagenase. The 1.7 kb DNA insert of pRS21 requires the presence of an extrinsic transcription-effecting sequence, such as the promoters described above, for transcription of the 68 kd form of collagenase.

Figure 3:
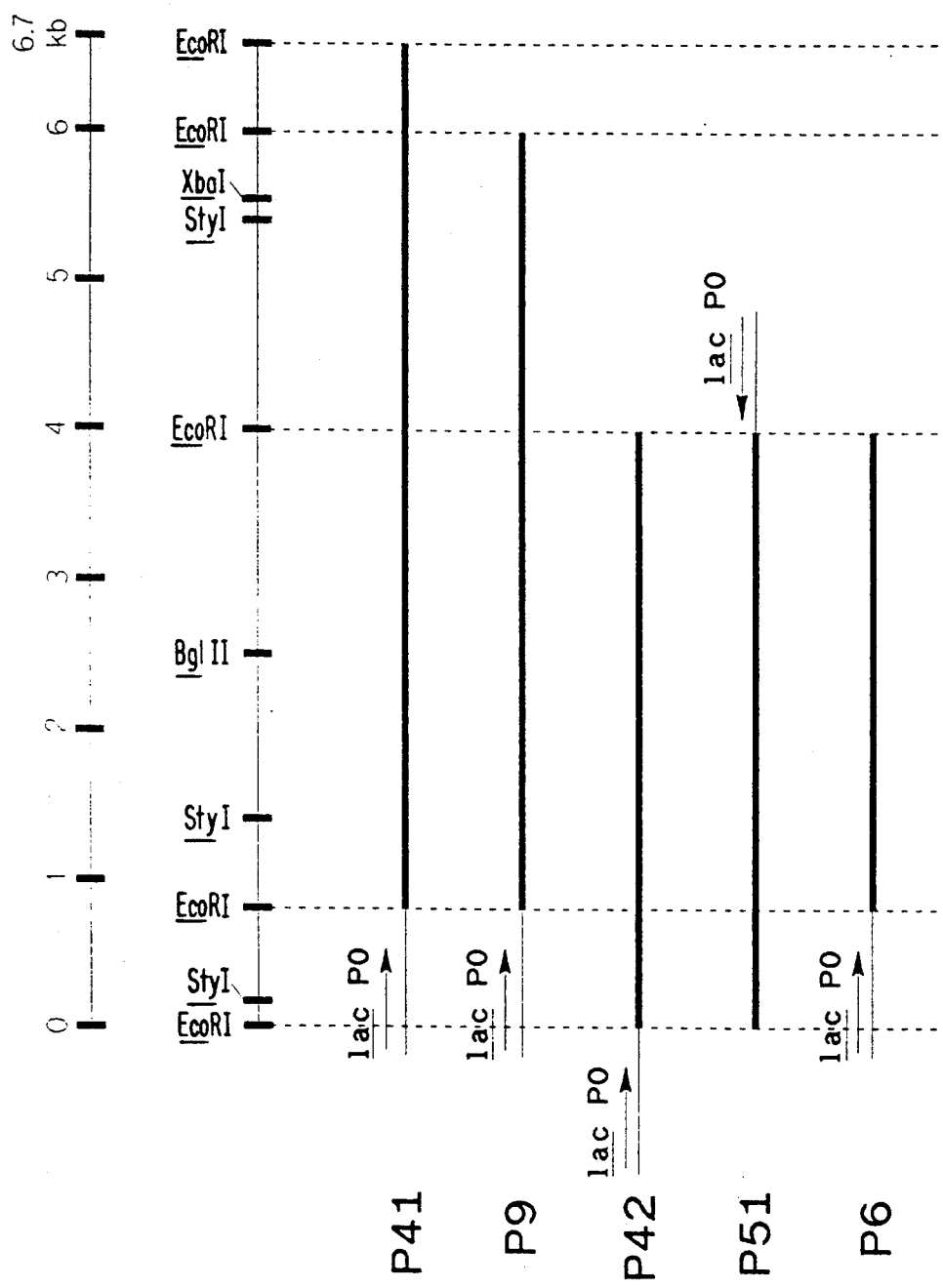
FIG. 3 shows the restriction maps of the plasmids containing the collagenase gene, showing the inserted *C. histolyticum* DNA.

The insert of pRS21 is close to the minimum size of DNA from which the 68 kd form of collagenase can be expressed. Other, larger, inserts also can express only the 68 kd form of collagenase. These include the inserts of plasmids P6, P9, and P41 (FIG. 3).

The insert of plasmid P6 is approximately 3.2 kb and is bounded by EcoRI sites. The insert includes single sites for StyI and BglII restriction enzymes. This insert does not code for the complete large form of collagenase, as it lacks a portion of the 5'-end of that gene. It does code for the 68 kd form, but requires the presence of an external promoter operatively linked to the insert.

The insert of plasmid P9 is approximately 5.2 kb and is also bounded by EcoRI sites. It includes the single StyI and BglII sites of the insert of P6, but extends further, so that it has an internal EcoRI site, an additional StyI site, and an XbaI site. This insert also requires an external promoter operatively linked with the insert to produce the 68 kd form of collagenase.

The insert of P41 is approximately 5.9 kb long and is the same as that of P9, except for the presence of an additional EcoRI fragment, so that it has two internal EcoRI sites. This insert also requires an external promoter.

2. Inserts Coding For Both 68 kd and Large Forms of Collagenase

Several classes of inserts code for both the 68 kd and the large form of collagenase. However, the form of collagenase that they actually produce depends on the arrangement of promoters with respect to the insert. These inserts include both primary cloned inserts and products of subcloning.

Two primary cloned inserts actually encode both forms of collagenase: the inserts of plasmids P42 and P51. These inserts include the same sequence of Clostridium DNA: a 4.0 kb segment bounded by EcoRI sites. The insert also includes an internal EcoRI site, two sites for StyI and one for BglII. However, the orientation of the Clostridium DNA segment relative to that of the lac promoter and operator is different in the two plasmids. In P42, the lac promoter is in the correct orientation to transcribe the collagenase gene; in P51, it is not. Accordingly, only in P42 are both the large form of collagenase and the 68 kd produced; in P51, only the 68 kd form of collagenase is produced. This is because the transcription of the large form of collagenase requires the presence of an outside promoter in proper orientation. i.e., fused contiguously to the Clostridium DNA (FIG. 3).

The insert of plasmid pBBI is also capable of producing both the large form of collagenase and the 68 kd form of collagenase. This plasmid is derived from P42 by subcloning: the DNA is cleaved at the single BglII site so that a 2.5 kb insert results. This insert produces both the large and 68 kd form of collagenase; at least 50% per weight of the collagenase protein produced is the 68 kd form.

Both the 68 kd collagenase and the large collagenase molecules react with and are precipitated by antibodies to β-collagenase. This result leads to the conclusion that both the 68 kd and large form of collagenase are translated from mRNA transcribed from the same stretch of DNA in the same reading frame. Otherwise, there would be no immunological cross-reactivity between the two polypeptides, even if two separate out-of-phase open reading frames existed. This result, however, leads to the completely unexpected conclusion that there exists a stretch of DNA within the 0.8 kd EcoRI segment that not only serves as the promoter for transcription of the 68 kd collagenase gene but is also translated into a portion of the large collagenase polypeptide.

B. Inserts Producing Fusion Peptides

Figure 7A:
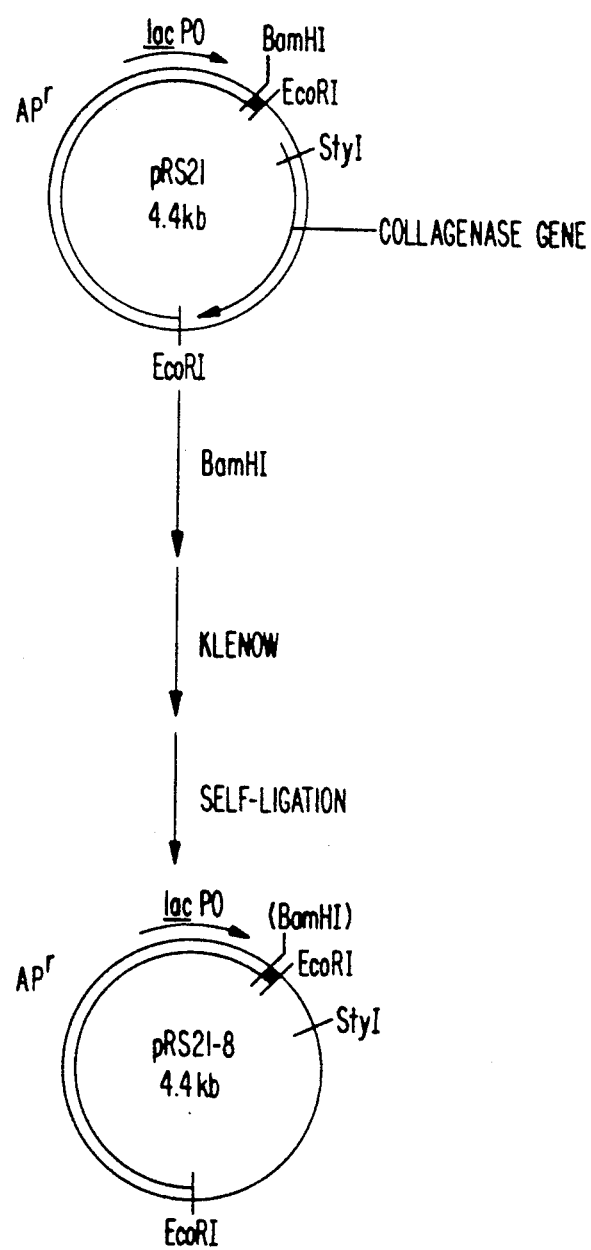
Figure 7B:
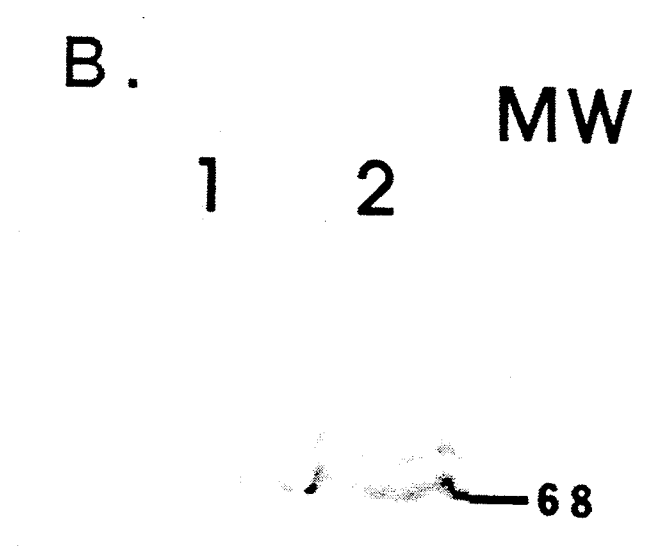

A second class of DNA inserts derived from Clostridium DNA contains a portion of the structural gene for Clostridium collagenase fused contiguously in an open reading frame with a structural gene derived from *E. coli*. The *E. coli* structural gene is typically the β-galactosidase gene, as in plasmid pRS21-8 (FIG. 7). Such inserts typically express two forms of collagenase: the 68 kd form of collagenase as described above and a larger fusion protein including a portion of the β-galactosidase gene. This fusion protein is distinguishable from the 68 kd form of collagenase on polyacrylamide gel electrophoresis by its larger size, having a molecular weight of at least 70,000 daltons. It is also immunoreactive, reacting with anti-collagenase antibody.

In this arrangement, the 68 kd form of collagenase is synthesized as a result of transcription activated by the Clostridium promoter that is located within the inserted DNA; the larger fusion peptide is under the control of the lac promoter, to which the segment of the β-galactosidase gene is operatively linked. The 68 kd form of collagenase is not linked to any protein derived from *E. coli*.

III. Plasmids Containing Inserts

A. λzao Plasmids

It is preferred to generate plasmids containing inserts by using the λzap system as described in J. M. Short, J. M. Fernandez, J. A. Sorge & W. D. Huse, "λzap: A Bacteriophage λ Expression Vector with in Vivo Excision Properties," *Nucl. Acids Res.* 16, 7583-7600 (1988). The λzap system allows ligated insert DNA packaged in vitro into a bacteriophage λ capsid to be rescued by single-stranded M13 bacteriophage to automatically produce "phagemid" particles containing the insert DNA (see Example 8). Plasmids produced by this process are capable of stably transforming *E. coli* cells and include at least one drug resistance marker and a replication origin enabling them to replicate autonomously.

B. Other Plasmid Vectors

Because the DNA inserts are bordered by EcoRI restriction endonuclease cuts, any cloning vector known in the art containing suitable EcoRI cloning sites can, alternatively, be used to generate plasmid vectors containing the inserted Clostridium collagenase DNA. Such vectors are capable of stably transforming *E. coli* and are selected from the group of vectors consisting of those with a drug resistance marker and a replication origin so that they can replicate independently of the *E. coli* chromosome. Suitable vectors include, but are not limited to pBR322 and its derivatives, including, but not limited to, pUC8, pUC9, pUC12, pUC13, pUC18, pUC19, and other vectors. Such vectors can be used to subclone DNA inserts originally obtained in λzap phagemids; pUC12 and pUC13 are especially preferred for subcloning.

Still other vectors such as λ Charon phages and cosmids are also usable for cloning. Many such vectors are well-known in the art and are described, for example, in B. Perbal, *A Practical Guide to Molecular Cloning* (2d ed., John Wiley, 1988), Ch. 6, "Vectors for Molecular Cloning."

IV. Production Of Inserts Containing Collagenase DNA

The DNA inserts containing collagenase DNA are produced by digestion of purified *C. histolyticum* chromosomal DNA with the restriction enzyme EcoRI. After digestion, the digested DNA is separated on a gel that can separate DNA fragments by size, such as an agarose gel, typically a 1% agarose gel. DNA fragments ranging from 2 kb to 10 kb are then electroeluted out of the gel and collected.

To determine which inserts carry the gene for collagenase, the library of in vitro packaged λ bacteriophage containing λ DNA is used to infect *E. coli* and the resulting phage plaques are screened by immunoblot screening (Examples 4 and 5). The phage from the positive plaques are then used to co-infect *E. coli* with M13 helper phages for the production of "phagemids" by an in vivo splicing process (Example 6).

V. Expression Of Collagenase

The expression of Clostridium collagenase genes in *E. coli* cells requires two steps: the transfection of the host *E. coli* cells with a suitable plasmid or other vector carrying the Clostridium DNA and detection of the collagenase produced by the transformed cells.

A Transformation of Host *E. coli* Cells

*E. coli* cells can be transformed with plasmids or other vectors that carry inserts of Clostridium DNA coding for either the large form or the 68 kd form of collagenase. Transformation of host *E. coli* cells is accomplished by standard procedures using $CaCl_2$ as described in D. Hanahan, *J. Mol. Biol.* 166. 557 (1983).

B. Collagenase Detection

Collagenase can be detected in *E. coli* cells transformed with plasmids by immunochemical techniques such as Western immunoblotting using anticollagenase antibody following separation of the products of in vivo protein translation by SDS-polyacrylamide gel electrophoresis. SDS-polyacrylamide gel electrophoresis is preferably performed according to the procedure described by U. K. Laemmli, "Cleavage of Structural Proteins During the Assembly of the Head of Bacteriophage T4," Nature 227, 680-685 (1970).

Western immunoblotting is also performed according to standard procedures known in the art, such as W. H. Burnette, "Western Blotting: Electrophoretic Transfer of Proteins from SDS-polyacrylamide Gels to Unmodified Nitrocellulose and Radiographic Detection with Antibody and Radioiodinated Protein A," *Anal. Biochem.* 112, 195-203 (1981). Other protocols for detection known in the art can alternatively be employed, such as in Vivo labeling of the synthesized protein with a radioisotope such as $^{35}S$ followed by immunoprecipitation. Such techniques are described, for example, in B. Perbal, supra, Ch. 25, "Expression of Cloned DNA Sequences in Vitro or in Procaryotic and Eucaryotic Cells," pp. 788-795.

2. Enzymatic Procedures

Cells transformed with plasmids according to the present invention unexpectedly produce enough active collagenase for it to be assayed with $^3H$-acetylated collagenase as substrate. Details are given in Example 13.

VI. Purification of Collagenase Produced By Genertically Engineered *E. Coli*

The 68 kd form of collagenase produced by genetically engineered *E. coli* can be substantially purified by standard enzyme purification procedures, especially those described in M. D. Bond & H. E. Van Wart, "Purification and Separation of Individual Collagenases of *Clostridium histolyticum* Using Red Dye Ligand Chromatography," Biochemistry 23, 3077-3084 (1984). Typically, purification can be carried out by a sequence of steps involving: (1) hydroxylapatite chromatography; (2) Sephacryl S-200 chromatography; (3) affinity chromatography on L-arginine-Affi-Gel 202 (Bio-Rad Laboratories, Richmond, Calif.); (4) chromatography on Reactive Red Dye 120-Agarose; and (5) ion-exchange chromatography on DEAE-cellulose. Other chromatographic procedures known in the art, such as high-pressure liquid chromatography (HPLC) can be used as additional steps or to replace particular steps of this procedure.

VII. Use of Collagenase Produced by Genertically Engineered *E. coli*

The purified collagenase produced by genetically engineered *E. coli* containing Clostridium DNA can be used for any application in which it is desired to digest collagen. Particular applications include: (1) digesting connective tissue and releasing embedded cells without destroying cell membranes and other essential structures; (2) isolating dispersed pancreatic islets; (3) dissociating tumors; and (4) intradiscal treatment of herniation of the nucleus pulposus ("slipped disc").

A. Use of Genetically Engineered Collagenase to Dissociate Tissue

A procedure for the use of genetically engineered collagenase to dissociate tissue comprises two steps.

In the first of these steps, the tissue to be dissociated is incubated in a buffered solution containing substantially purified genetically engineered collagenase at about 25° C. to about 37° C. with shaking. This step serves to release and disperse the cell type to be collected. The pH is typically within a range of about 6.0 to 8.5, more preferably within in a range of about 7.0 to 8.0, most preferably about 7.5. The tissue to be dissociated can be, but is not limited to, connective tissue, pancreatic tissue, or tumor tissue.

In the second step, the cells to be collected are separated from tissue debris. This separation step is typically performed by density gradient centrifugation.

This procedure can digest connective tissue and release embedded cells, isolate dispersed pancreatic islets from pancreatic tissue, or dissociate tumors and isolate tumor cells from them.

B. Use of Genetically Engineered Collagenase to Treat Herniated Nucleus Pulposus ("Slipped Disc")

Genetically engineered collagenase can be used to treat herniated nucleus pulposus, known to the lay person as "slipped disc," and other similar types of disc damage. The treatment method comprises the steps of:

(1) preparing a sterile buffered solution containing substantially purified genetically engineered Clostridium collagenase; and (2) injecting the sterile buffered solution containing the substantially purified collagenase into the nucleus pulposus.

EXAMPLES

The following examples are for illustrative purposes only and are not to be construed as limiting the invention.

EXAMPLE 1

Autocatalytic Degradation of Collagenase Purified from Clostridium by Conventional Techniques Five forms of Clostridium collagenase were purified to greater than 90% purity—$\beta$, $\gamma$, $\eta$, $\xi$, and $\zeta$—by using the procedure of M. D. Bond & H. E. Van Wart, "Purification and Separation of Individual Collagenases of *Clostridium histolyticum* Using Red Dye Ligand Chromatography," Biochemistry 23, 3077-3085 (1984), with minor modifications.

Crude collagenase obtained from Sigma Chemical Co. (St. Louis, Mo.) was first resuspended in 0.05 M phosphate buffer, pH 6.7. After the undissolved material was removed by centrifugation, the proteins were separated by sequentially chromatographing them through hydroxylapatite, Sephacryl™ S-200 (Pharmacia, Uppsala, Sweden), arginine-Sepharose™ (Pharmacia), and Reactive Red 120 dye resin (Sigma). The individual collagenases were then purified by DEAE-cellulose and/or SP-Sephadex™ (Pharmacia) to separate the individual forms of collagenase.

The molecular weights of the purified collagenases were determined by SDS-polyacrylamide gel electrophoresis according to the method of Laemmli (U. K. Laemmli, "Cleavage of Structural Proteins During the Assembly of the Head of Bacteriophage T4," Nature 227, 680-685 (1970)). The results are shown in FIG. 1. The molecular weights of the purified collagenases were as follows: $\beta$, 115 kd; $\gamma$, 79 kd; $\eta$, 130 kd; $\xi$, 110 kd; and $\zeta$, 125 kd.

Following purification to homogeneity (FIG. 1), the purified collagenases were stored individually at $-80°$ C. for two months and re-examined after electrophoresis by staining with Coomassie brilliant blue and by immunoblotting. In all cases, multiple degradation products were seen (FIG. 2). This result indicates that proteolytic autodegradation of the original purified collagenases occurred during storage, even at $-80°$ C. As indicated by the similarities between the Coomassie brilliant blue stain patterns (FIG. 2A) and the immunoblotting patterns (FIG. 2B), many, though not all, of the degradation products cross-reacted with the antibody to purified $\beta$-collagenase (Example 4, below).

EXAMPLE 2

Production of Antibody to $\beta$-Collagenase

A preparation of purified $\beta$-collagenase was used to prepare antibodies. Beta-collagenase (600 µg) was mixed with Freund's complete adjuvant and injected into the back and both thighs of New Zealand rabbits. Once every three-week interval, antibody production was boosted with an injection of 600 µg of $\beta$-collagenase in Freund's incomplete adjuvant. Sera were collected after two booster injections. The antibody titers were determined by immunoblotting, and the cross-reactivity to collagenases other than β-collagenase was similarly examined by immunoblotting. The antiserum cross-reacted efficiently with η-, γ-, ζ-, and ξ-collagenases (FIGS. 1B and 2B).

The antiserum also reacted against many of the autolytic degradation products of the collagenases. However, in some cases, certain degradation products were only recognized when the class of the collagenase from which they originated was the same as that of β-collagenase (Class I according to the Bond and Van Wart classification). For example, a 46-kd degradation product was generated from both β-collagenase and ζ-collagenase (Class II), but only the 46-kd degradation product generated from the β-collagenase was recognized by the antibody (FIGS. 2A and 2B, lanes 1 and 5). Similarly, a 33-kd degradation product from the Class II ξ-collagenase did not react with the anti-β-collagenase antibody (FIG. 2B, lanes 3 and 5). This makes possible a distinction between Class I and Class II collagenases based upon the immunoreactivity of their degradation profiles.

The ability of this antibody to interact with both classes of collagenase made it suitable for screening a bacteriophage λ library for clones containing collagenase genes.

EXAMPLE 3

DNA Isolation from Clostridium histolyticum

*Clostridium histolyticum* strain ATCC 21000 was obtained from the American Type Culture Collection. The paper tablet containing the bacteria was first soaked in TYE broth (15 g tryptone, 10 g yeast extract, and 5 g NaCl per liter of culture medium) for 30 minutes at 4° C. with occasional shaking.

The cell suspension was streaked on a TYE agar plate and grown at 37° C. under anaerobic conditions. A single colony was picked and grown in 50 mL TYE broth and grown at 37° C. under anaerobic conditions. The cells were collected by centrifugation and resuspended in TES (0.1 M Tris, pH 8.0, 0.1 mM EDTA, and 0.15 M NaCl). Lysozyme was added to a final concentration of 100 μg/mL and the suspension incubated at 4° C. for 1 hour.

Cells were partially lysed by freezing and thawing the cell suspension four times. SDS and pronase K were then added to final concentrations of 0.5% and 200 μg/mL, respectively. The cell debris was removed by centrifugation at 10,000 rpm in a Beckman J2-21 centrifuge for 30 minutes at 4° C. The supernatant was extracted three times with equal volumes of phenol-chloroform, and the DNA was precipitated with isopropanol. DNA concentration was measured by electrophoresing the DNA through an agarose gel and comparing fluorescence after the addition of ethidium bromide with the fluorescence of a known concentration standard. The average size of purified Clostridium DNA was measured by electrophoresis on a 0.6% agarose gel and was 30 kb to 40 kb.

EXAMPLE 4

Construction of Bacteriophage λ Library Containing Inserted Clostridium DNA Purified *C. histolyticum* chromosomal DNA (Example 3) was partially digested with restriction endonuclease EcoRI. The fragments resulting from restriction endonuclease digestion were separated on a 1% agarose gel. DNA fragments of sizes from 2 to 10 kb were electroeluted out of the gel and collected and precipitated with ethanol. The DNA was resuspended in TE buffer (10 mM Tris, pH 7.4, 0.1 mM EDTA). Appropriate amounts of the isolated DNA were ligated with bacteriophage λzap DNA (J. M. Short, J. M. Fernandez, J. A. Sorge & W. D. Huse, "λzap: A Bacteriophage λ Expression Vector with in Vivo Excision Properties," *Nucl. Acids Res.* 16, 7583–7600 (1988)) that had been cleaved with EcoRI and then treated with alkaline phosphatase. The ligation was performed at 4° C. for 16 hours. Bacteriophage λzap, a derivative of phage λ, can clone DNA inert sizes up to 10 kb. It contains the lac promoter and part of the 5′-end of the β-galactosidase structural gene with multiple cloning sites within the gene. This system provides a positive selection for the clones containing the insert DNA. Bacteriophage λzap also contains an in vivo splicing signal that can excuse a "phagemid" DNA from the λzap DNA. The phagemid DNA can then be packaged in vivo into the protein coat of bacteriophage M13 to become a filamentous phage particle. The phage particle carrying the single-stranded plasmid DNA can then infect susceptible bacteria, after which the single-stranded plasmid DNA is then converted to double-stranded plasmid DNA by the same mechanism used to convert single-stranded M13 phage DNA to double-stranded replicative form DNA. The λzap system provides a useful tool to convert the cloned DNA within λ directly into a plasmid without the necessity of a tedious subcloning step.

The DNA ligated into λzap DNA was then packaged in vitro into phage λ particles using phage λ lysate (Stratagene Cloning Systems, La Jolla, Calif.). Phage particles that were packaged in vitro were then used to infect *E. coli* strain BB4 (sup F58, sup E44, hsd R514 (rk−, mk+), gal K2, gal T22, trp R55, met B1, ton A, lambda−, Δ (arg-lac) U169 [F′, pro AB, lac I$^q$ZΔM 15, Tn 10 (tet$^R$)] to determine the efficiency of packing, frequency of recombinants, and insert sizes. The library was amplified to a working library and stored at −80° C. About $5 \times 10^5$ primary plaques were generated by the in vitro packaging process of which about 80% or $4 \times 10^5$ plaques had inserted Clostridium DNA. The average insert size of the primary library as determined by the analysis of insert size of 20 randomly picked clones was approximately 4 kb. Although the genome size of Clostridium is not known, it is assumed to be roughly equivalent to that of the *E. coli* genome ($4 \times 10^6$ bp). With an average size of 4 kb, 4600 individual clones are sufficient to cover the entire gene with 99% confidence. The actual library should be able to cover a genome greater than $3 \times 10^8$ bp with 99% confidence. Therefore, the actual library is sufficient to represent the Clostridium genome.

EXAMPLE 5

Screening of Bacteriophage λ Library of Example 4

Approximately 10,000 plaque-forming units (pfu) of bacteriophage λ from Example 4 were used to infect *E. coli* strain XL1-Blue (end A1, hsd R17 (rk−, mk+), Sup E44, thi-1, lambda−, rec A1, gry A96, rel A1, (lac−) [F′, pro AB, lac I$^q$ZΔM 15, Tm 10 (tet$^R$)]). The infected bacteria was mixed with 3 mL of TYE-soft agarose containing MgCl$_2$ and maltose and poured as an overlay into a petri dish containing TYE agar. Dried nitrocellulose paper previously soaked in 1 mM IPTG was placed on top of the plate after it was incubated at 37° for 5 hours or until plaques could be visualized. After overnight incubation, the nitrocellulose paper was lifted from the petri dish and used for immunoblot screening. The nitrocellulose paper was incubated with the rabbit anti-collagenase antibody of Example 2 at a dilution of 1:1000 with 5% skim milk at room temperature for 1 hour, washed with 0.1 M Tris-HCl buffer, pH 8.0, containing 0.2 M NaCl and 1% Triton ™ X-100, then incubated with protein A-horseradish peroxidase conjugate at 1:1000 dilution in PBS with 5% skim milk at room temperature for 1 hour. The washing procedure was repeated and the nitrocellulose paper developed with 4-chloro-1-naphthol and $H_2O_2$ in PBS as described in R. A. Young & R. W. Davis, "Efficient Isolation of Genes by Using Antibody Probes," *Proc. Natl. Acad. Sci. USA* 80, 1194–1198 (1983). The area of agarose on the plate corresponding to the location of a positive signal on the nitrocellulose was soaked with SM buffer (0.1 M NaCl, 0.01 M $MgSO_4$, 100 mg/L gelatin, and 0.02 M Tris-HCl, pH 7.5) to release the phage as described in T. V. Huynh, R. A. Young & R. W. Davis, "Constructing and Screening cDNA Libraries in λgt10 and λgt11" in *DNA Cloning*, vol. III. D. M. Glover, ed. (IRL Press, Oxford), pp. 749–789. Up to 5 positive plaques per plate were identified. The area of each positive plaque was picked and rescreened under conditions of lower plaque density (~100 plaques per plate) until each individual positive plaque was free of contaminants. More than 25 positive plaque areas were identified and purified by this procedure. Plaque lysates from several clones were randomly collected and run directly on a 7.5% SDS-polyacrylamide gel, then reacted with the anticollagenase antibody of Example 2. Immunoreactive protein bands ranging from about 68 to 100 kd were detected.

EXAMPLE 6

In Vivo Splicing of the Recombinant Phages

In order to characterize the DNA inserts, the recombinant λ phages underwent in vivo splicing to become phagemids. The recombinant phages isolated from individual plaques were used to co-infect *E. coli* strain XL1-Blue along with M13R408 helper phage ((M. Russel, S. Kidd & M. R. Kelly, "An Improved Filamentous Helper Phage for Generating Single-stranded Plasmid DNA." *Gene* 45, 333–338 (1986)). The infected bacteria were grown in TYE broth containing 10 mM $MgCl_2$ for 3 hours at 37° C. The culture broth was heated at 70° C. for 20 minutes, then centrifuged for 5 minutes at 4,000 xg to collect the supernatant. The supernatant contained the phagemid DNA packaged as filamentous phage particles. This phage stock was used to infect *E. coli* strain XL1-Blue, plated on TYE-Ap plates, and incubated overnight at 37° C. The colonies appeared to contain the phagemid vector with the inserted DNA and with no bacteriophage λ DNA. Twenty-five separate clones were isolated containing inserted Clostridium DNA.

EXAMPLE 7

Restriction Endonuclease Analysis of Inserted DNA

DNA from each clone of Example 6 was isolated by alkali as described by T. Maniatis, E. F. Fritsch & J. Sambrook, "Molecular Cloning: A Laboratory Manual" (Cold Spring Harbor Laboratory Press, Cold Spring Harbor, N.Y., 1982). Insert sizes were initially verified by EcoRI digestion. Five different patterns of digestion by EcoRI were identified among the 25 independently isolated clones, according to the number and size of the EcoRI fragments generated. All of the inserts were found to contain a 3.2 kb EcoRI fragment, indicating that this fragment may contain all or part of the collagenase gene. These five different patterns are described herein by the designation of one of the plasmids exhibiting the pattern, such as P42.

A more detailed restriction map was prepared for the plasmid representing each of the five classes of inserts by digestion with the restriction endonucleases BamHI, BglII, StyI, and XbaI, using plasmid DNA purified through a CsCl density gradient. These maps are shown in FIG. 3. When the restriction endonuclease maps from all of these classes are combined, the total extent of Clostridium DNA cloned was about 6.5 kb. This length of DNA is included within four EcoRI fragments. No single insert contains the full extent of this cloned DNA; the size of the cloned Clostridium DNA varies among the five groups from approximately 4 kb (P42) to approximately 5.9 kb (P41). The names of the plasmids that represent each of these groups are shown in FIG. 3. Two of these groups, P42 and P51, contain the same EcoRI fragments but in opposite orientations relative to the lac promoter and operator, as shown in FIG. 3.

EXAMPLE 8

Immunoreactivity of Proteins Produced by Cells Transformed with Plasmids Containing Clostridium DNA Inserts Lysates of bacteria transformed by the plasmids containing Clostridium DNA inserts were subjected to immunoblotting after transcription from the lac promoter was activated. The cells carrying the plasmids were grown in TYE-Ap broth and induced with 1 mM IPTG for 4 hours. The cells were collected by centrifugation and resuspended in 10 mM phosphate buffer, pH 7.4, with 1 mM PMSF. An appropriate volume of cell suspension was mixed with gel loading buffer, heated, and run on a 7.5% or 11.25% SDS-polyacrylamide gel as described in the Nature article by Laemmli. The proteins were electroblotted to unmodified nitrocellulose paper and detected with the rabbit anticollagenase antibody of Example 2 as described in W. H. Burnette, "Western Blotting: Electrophoretic Transfer of Proteins from SDS-polyacrylamide Gels to Unmodified Nitrocellulose and Radiographic Detection with Antibody and Radioiodinated Protein A," *Anal. Biochem.* 112, 195–203 (1981). The molecular weight of the collagenase from the different clones was determined by comparison with prestained protein standards.

Figure 4:
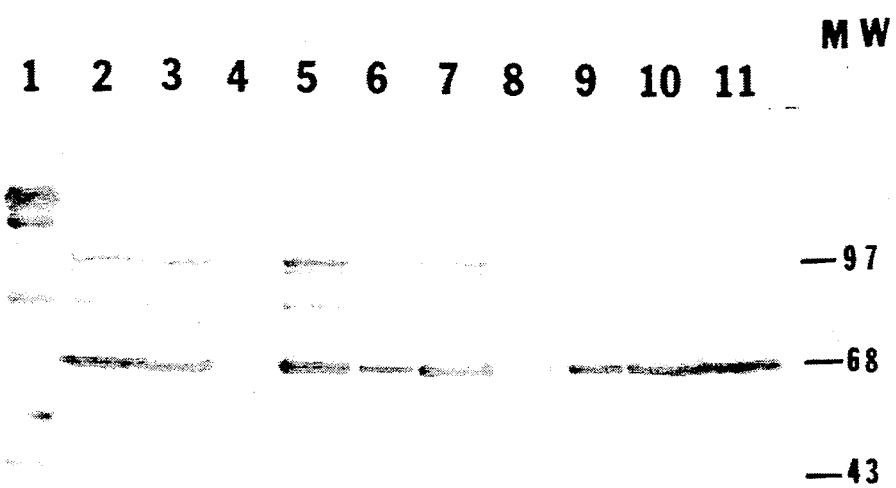
FIG. 4 shows the results of Western blotting of lysates of *E. coli* strain XL1-Blue transformed with different plasmids carrying different inserts.

The results are shown in FIG. 4. The group of clones with the restriction pattern equivalent to that P42 produced multiple immunoreactant bands with molecular weights ranging from 68 kd to about 100 kd. Clones with the remaining four restriction patterns (P41, P9, P51, and P6) produced only a 68 kd immunoreactive protein band.

EXAMPLE 9

Subcloning of Plasmid P42

Figure 5:
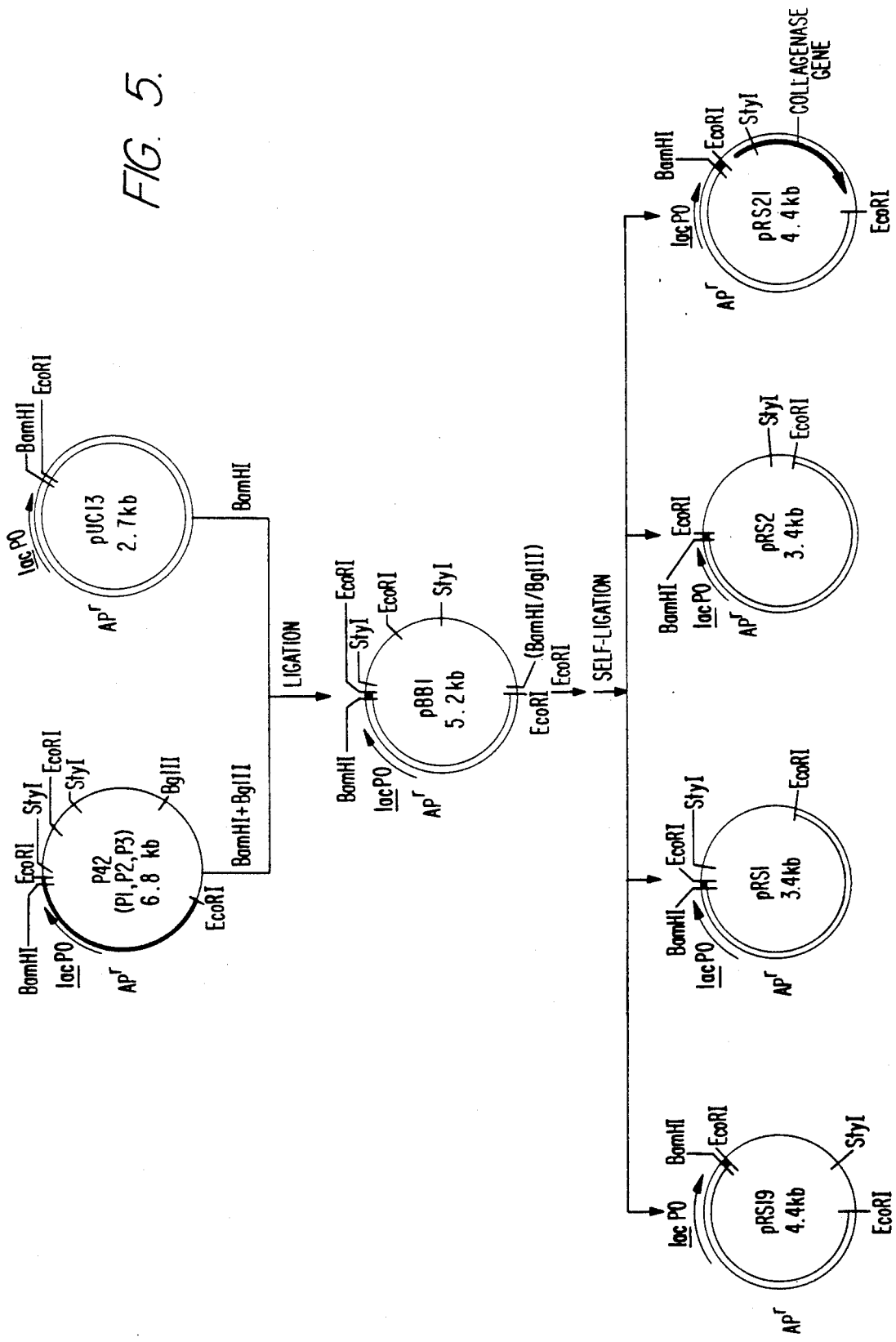
FIG. 5 shows the scheme of subcloning used to isolate the segment of Clostridium DNA coding for the 68 kd form of collagenase.
Figure 6:
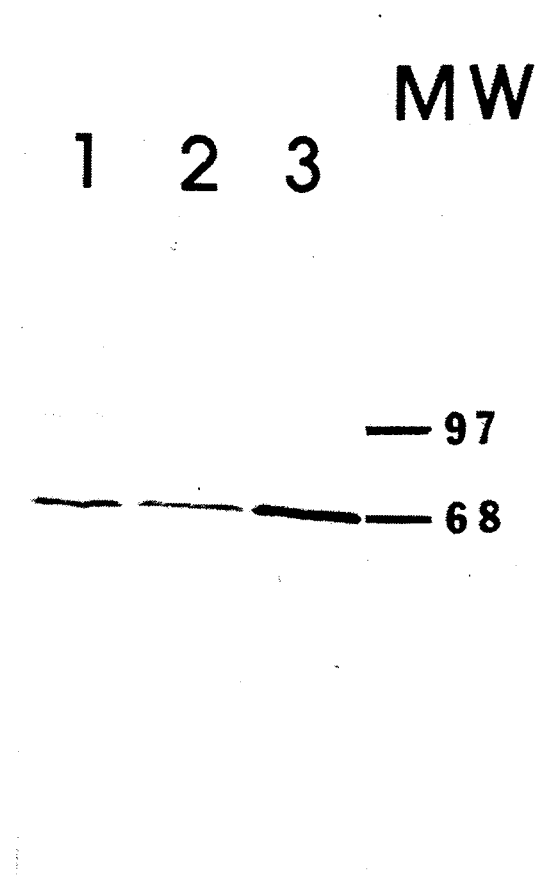

Plasmid P42 was subjected to further subcloning to understand the location and the orientation of the Clostridium collagenase genes. Plasmid P42 DNA was digested with BglII and Bam HI restriction endonucleases and then ligated with plasmid pUC13 that had been linearized by digestion with Bam HI. A plasmid, pBB1, that contained a 2.5 kb Clostridium DNA segment derived from the Clostridium DNA segment of plasmid P42 was isolated (FIG. 5). Cell lysate was prepared from IPTG-induced E. coli strain XLI-Blue transformed with pBB1 and subjected to Western immunoblotting as in Example 8. The results are shown in FIG. 6. The immunoblotting pattern was similar to that obtained from plasmid P42, with several bands ranging in molecular weight from 68 kd to about 100 kd.

EXAMPLE 10

Further Subcloning of Plasmid pBB1

In order to characterize the organization of the Clostridium DNA in plasmid pBB1 more precisely, pBB1 was subjected to further subcloning by digestion with EcoRI and self-ligation. The 2.5 kb Clostridium insert of pBB1 consists of two EcoRI fragments, one of 1.7 kb and a second of 0.8 kb. Four clones containing only one of these two EcoRI fragments in different orientations relative to the orientation of the lac promoter present in the plasmid: pRS19 and pRS21 with the 1.7 kb EcoRI fragment, and pRS1 and pRS2 with the 0.8 kb EcoRI fragment. These plasmids are shown in FIG. 5.

Of these four plasmids containing single EcoRI fragments, only pRS21 generated material immunoreactive with the anticollagenase antibody in the Western immunoblotting test. The plasmid pRS19, which contains the 1.7 kb fragment in the opposite orientation, relative to the lac promoter, to the orientation in pRS21, did not produce any immunoreactive material. The lac promoter in plasmid P42 and in all plasmids derived from it by subcloning is located next to the insert and transcribes mRNA toward the insert. Therefore, only a gene that is located downstream from the lac promoter in the correct orientation produces immunoreactive material.

The fact that the production of immunoreactive material requires the presence of a lac promoter in the correct orientation when the 0.8 kb EcoRI fragment is removed strongly suggests that the 0.8 kb EcoRI contains a functioning promoter from which transcription of the mRNA for the 68 kd immunoreactive peptide can be initiated. However, the structural gene for this 68 kd immunoreactive peptide is entirely located in the 2.5 kb fragment.

EXAMPLE 11

Demonstration That the 4 kb Insert of Plasmid P42 Contains the Intact 5'-end of the Collagenase Gene Insertion of four bases near the 5'-end of the 4 kb Clostridium DNA insert of plasmid P42 was used to demonstrate that P42 contained the intact 5'-end of the collagenase gene. Plasmid P42 was first digested with Bam HI, which cuts the sequence

```
GGATCC
CCTAGG
``` leaving four-base "sticky ends" with the sequence GATC. These sticky ends were filled in with the Klenow fragment of E. coli DNA polymerase I and self-ligated. This procedure inserts four extra nucleotides into the sequence between the 5'-end of the β-galactosidase gene and the inserted Clostridium DNA. Because the genetic code is translated in groups of three bases, such an insertion has the effect of altering the reading frame and preventing inframe translation past the position of the insertion.

Following this process of addition of the four bases, the altered plasmid still produced the same pattern of immunoreactive material as the original P42 plasmid. This result supports a conclusion that the Clostridium DNA insert of P42 contains the intact 5'-end of the collagenase gene.

EXAMPLE 12

Demonstration That the Production of the Immunoreactive, 68 kd Protein Does Not Require the 5'-end of the Collagenase Gene An experiment similar in design to that of Example 11 was performed to determine how the 68 kd immunoreactive protein is produced from the subcloned plasmid pRS21. Plasmid pRS21 was digested with Bam HI restriction endonuclease. The sticky ends were filled in with the Klenow fragment of E. coli DNA polymerase I and self-ligated. If the 68 kd immunoreactive protein produced by pRS21 had been a fusion protein beginning in the β-galactosidase gene, in-frame translation would be prevented by the addition of the four bases and the 68 kd protein would not be produced.

The results are shown in FIG. 7. The 68 kd immunoreactive protein was still produced after the four bases were added. In addition, an extra immunoreactive protein band slightly larger than the 68 kd protein band was seen. This second band most likely represented a fusion protein starting from the β-galactosidase gene and continuing into the 68 kd collagenase gene. The addition of the four bases generated an open reading frame. This result also provides evidence that the same DNA fragment can be used to synthesize more than one protein.

EXAMPLE 13

Assay of Collagenase Activity in Transformed Cells

E. coli cells transformed with various plasmids containing the Clostridium collagenase gene were lysed. The lysates were partially purified by chromatography through DE-52 cellulose (DEAE-cellulose) and then through CM-52 cellulose (carboxymethyl-cellulose). The partially purified collagenase was assayed with PZ-Pro-Leu-Gly-Pro-D-Arg as substrate as described by E. Wünsch & H. G. Heidrich, Hoope-Seyler's Z. Physiol. Chem. 333, 149–151 (1963). Only weak collagenase activity was detected with this assay.

Therefore, a more sensitive collagenase assay was used with $^3$H-acetylated collagen as substrate and crude lysate as enzyme, as described in S. K. Mallya, K. A. Mookhtiar, & H. E. Van Wart, "Accurate Quantitative Assays for the Hydrolysis of Soluble Type I, II, and III $^3$H-acetylated Collagen by Bacterial and Tissue Collagenases," Anal. Biochem. 158, 334–0345 (1986). To produce the crude lysate used as the source of enzyme in the assay, the E. coli strains carrying the plasmids were each grown in 10 mL of culture medium and induced with 1 mM IPTG overnight. The cells were collected by centrifugation and resuspended in 300 μL of 10 mM Tris, pH 7.5, 1 mM PMSF, 1 mM EDTA. Lysozyme was added to a final concentration of 100 μg/mL and the suspension was incubated on ice for 30 minutes. The cell suspension was mixed gently and the supernatant was collected by centrifugation. MgCl$_2$ was added to 10 mM.

To perform the assay, lysate containing collagenase (50 μL) was incubated with 950 μL of digestion buffer (50 mM Tricine, 0.2 mM NaCl, 10 mM $CaCl_2$) containing 100 μg of $^3$H-acetylated collagen at 25° C. Aliquots were removed at 0, 0.5, 1, 2, 3, 4, and 5 hours after the start of incubation to an Eppendorf tube containing 50 μL of 20 mM 1,10-phenanthroline to quench the reaction. The tubes were immediately mixed vigorously and incubated at 30° C. for 10 minutes. Next, 150 μL of dioxane at 23° C. was added while the tubes were still in the water bath, and the tubes were mixed vigorously, chilled on ice for 10 minutes, and centrifuged at 4° C. for 10 minutes at 12,000 xg. Aliquots of the supernatant (150 μL) were transferred to a vial containing 5 mL of scintillation fluid and counted. The cpm released for each time point were plotted versus time and compared to a known standard of purified β-collagenase to determine the quantity of collagenase present.

The results are shown in Table I. All of the transformed strains produced detectable collagenase activity, but no collagenase activity was seen when *E. coli* cells transformed by the cloning vector alone was used as a source of lysate. Additionally, all collagenase activity was abolished when 5 mM 1,10-phenanthroline and 10 mM EDTA were added. This combination of reagents is a specific collagenase inhibitor. These results indicate that active collagenase with the characteristics of Clostridium collagenase was produced in the transformed cells.

TABLE I

ANALYSIS OF COLLAGENASE ACTIVITY IN *E. COLI* LYSATE[a]

| PLASMID | *E. coli* STRAIN | MEDIUM | [Collagenase][b] (μg/ml) |
|---|---|---|---|
| pbluescript[c] | DH5α | Min-Ap[d] | 0 |
| P6 | DH5α | Min-Ap | 0.28 |
| P9 | DH5α | Min-Ap | 0.24 |
| P41 | DH5α | Min-Ap | 1.8 |
| P42 | DH5α | Min-Ap | 0.47 |
| P51 | DH5α | Min-Ap | 1.0 |
| P42 | XL1-Blue | TYE-Ap | 3.0 |
| P51 | XL1-Blue | TYE-Ap | 0.95 |
| pBB1 | XL1-Blue | TYE-Ap | 1.0 |
| pRS21 | XL1-Blue | TYE-Ap | 2.5 |

[a] *E. coli* strains carrying different plasmids were grown in 10 ml culture medium and induced with 1 mM IPTG overnight at 37° C. and the cells were collected by centrifugation. The cells were resuspended in 300 μl of 10 mM Tris, pH 7.5, 1 mM PMSF, 1 mM EDTA. Lysozyme was added to a final concentration of 100 μg/ml and incubated on ice for 30 minutes. The cell suspension was vortexed and supernatant was collected by centrifugation and then supplemented with 10 mM $MgCl_2$. 50 μl of supernatant was used to determine the enzyme activity using $^3$H-acetylated collagen substrate and described (21).
[b] The collagenase quantities are calculated based on assuming these collagenases have the same specific activity as β-collagenase.
[c] The cloning vector, used as negative control.
[d] Min-Ap: minimal medium supplemented with 100 μg/ml Ap.

ADVANTAGES OF THE INVENTION

The present invention achieves the cloning of a single form of *Clostridium histolyticum* collagenase free from other forms of collagenase or other Clostridium proteins. This provides a useful method for the production of uniform preparations of unlimited quantities of a single form of genetically engineered collagenase by transformed *E. coli* cells without the presence of other contaminating Clostridium proteases. This collagenase preparation is especially advantageous because it is not subject to autocatalytic degradation, making it especially desirable for use in pancreatic islet isolation, as well as suitable for other uses of collagenase.

Although the present invention has been described in considerable detail with regard to certain preferred versions thereof, other versions are possible. Therefore, the spirit and scope of the appended claims should not be limited to the descriptions of the preferred versions contained herein.

What is claimed is:

1. An isolated and purified recombinant DNA fragment consisting essentially of DNA derived from *Clostridium histolyticum* coding solely for a polypeptide having the enzymatic activity of *C. histolyticum* collagenase, the polypeptide having a molecular weight of about 68,000 daltons.

2. The DNA fragment of claim 1 capable of being transcribed to yield mRNA, the mRNA being capable of being translated to yield a polypeptide of about 68,000 daltons molecular weight and having collagenase activity, the polypeptide being distinguishable by the heterologous expression of the sequence of claim 3 from the endogenous production by *C. histolyticum* of mutliple forms of collagenase by the essential absence of those forms of *C. histolyticum* collagenase having molecular weights of above about 70,000 daltons determined by the expression of the *C. histolyticum* genomic coding sequence.

3. The DNA fragment of claim 1 capable of being transcribed to yield mRNA, the mRNA being capable of being translated to yield a peptide displaying the antigenicity of *C. histolyticum* collagenease, the polypeptide being distinguishable by the heterologous expression of the sequence of claim 3 from the endogenous production by *C. histolyticum* of multiple forms of collagenase by the essential absence of those forms of *C. histolyticum* collagenase having molecular weights of above about 70,000 daltons determined by the expression of the *C. histolyticum* genomic coding sequence.

4. The DNA fragment of claim 2 wherein the DNA derived from *C. histolyticum* contains a promoter within the inserted Clostridium DNA such that the DNA can be transcribed under control of the promoter to yield mRNA capable of being translated to yield the polypeptide of about 68,000 daltons without the functioning of a promoter external to the DNA derived from *C. histolyticum*.

5. A DNA fragment comprising the DNA fragment of claim 2 fused contiguously to a transcription-effecting DNA sequence selected from the group consisting of *Escherichia coli* lac promoter, *E. coli* trp promoter, bacteriophage λ $P_L$ promoter, and tac promoter such that the transcription-effecting sequence can effect transcription of the DNA derived from *C. histolyticum*.

6. A DNA fragment comprising the DNA fragment of claim 4 fused contiguously at least a portion of the structural gene for *E. coli* β-galactosidase, the portion of the structural gene for β-galactosidase being operatively linked to a lac promoter such that:

(i) the DNA derived from Clostridium can be transcribed under control of the promoter located within the Clostridium DNA to yield mRNA capable of being translated to yield the polypeptide of about 68,000 daltons without the functioning of a promoter external to the DNA derived from *C. histolyticum*; and (ii) the Clostridium DNA fused to the DNA sequence comprising at least a portion of the structural gene for *E. coli* β-galactosidase can be transcribed under control of the lac promoter to yield mRNA capable of being translated to yield a fusion polypeptide of molecular weight greater than 70,000 daltons displaying the antigenicity of *C. histolyticum* collagenase and containing at least a portion of the amino acid sequence of *E. coli* β-galactosidase.

7. A vector comprising the DNA fragment of claim 4 incorporated into a plasmid capable of stably transforming *E. coli* host cells selected from the group of plasmids consisting of those with both a drug resistance marker and a replication origin.

8. The vector of claim 7 wherein the plasmid is generated in vivo by rescue of λzap DNA containing the inserted Clostridium DNA by M13 helper phage.

9. A vector comprising the DNA fragment of claim 5 incorporated into a plasmid capable of stably transforming *E. coli* host cells selected from the group of plasmids consisting of those with both a drug resistance marker and a replication origin.

10. The vector of claim 9 wherein the plasmid is generated in vivo by rescue of λzap DNA containing the inserted Clostridium DNA by M13 helper phage.

11. A vector comprising the DNA fragment of claim 8 incorporated into a plasmid capable of stably transforming *E. coli* host cells selected from the group of plasmids consisting of those with both a drug resistance marker and a replication origin.

12. The vector of claim 11 wherein the plasmid is generated in vivo by rescue of λzap DNA containing the inserted Clostridium DNA by M13 helper phage.

13. An isolated and purified recombinant DNA fragment comprising:
    (a) a *Clostridium histolyticum* structural gene encoding *C. histolyticum* collagenase and capable of being transcribed to yield mRNA capable of being translated to yield polypeptides of molecular weight of from about 70,000 dalonts to about 100,000 daltons and having the enzymatic activity of *C. histolyticum* collagenase; and
    (b) an internal promoter located within the structural gene of (a) and operatively linked to a Clostridium DNA sequence comprising a portion of the structural gene of (a) and capable of being transcribed to yield mRNA capable of being translated to yield a polypeptide of about 68,000 daltons molecular weight, the polypeptide having collagenase activity, the polypeptide being distinguishable by the heterologous expression of the sequence of claim 3 from the endogenous production by *C. histolyticum* of multiple forms of collagenase by the essential absence of those forms of *C. histolyticum* collagenease having molecular weights of above about 70,000 daltons determined by the expression of the *C. histolyticum* genomic coding sequence; the internal promoter being positioned such that the DNA sequence of (b) can be translated independently of the structural gene of (a).

14. A DNA fragment comprising the DNA fragment of claim 13 fused contiguously to a transcription-effecting DNA sequence selected from the group consisting of *E. coli* lac promoter, *E. coli* trp promoter, bacteriophage λ P$_L$ promoter, and tac promoter such that the transcription-effecting sequence can effect transcription of the structural gene of (a).

15. The DNA of claim 14 wherein the *C. histolyticum* structural gene of (a) and DNA sequence of (b) are capable of being alternatively and colinearly expressed to produce *C. histolyticum* collagenase having molecular weights ranging from about 68,000 daltons to about 100,000 daltons.

16. The DNA fragment of claim 15 wherein the internal promoter of (b) is capable of coding for and being read as an internal amino acid sequence of the structural gene of (a).

17. A vector comprising the DNA fragment of claim 14 incorporated into a plasmid capable of stably transforming *E. coli* host cells selected from the group of plasmids consisting of those with both a drug resistance marker and a replication origin.

18. The vector of claim 17 wherein the plasmid is generated in vivo by rescue of λzap DNA containing the inserted Clostridium DNA by M13 helper phage.

19. *E. coli* host cells transformed with the vector of claim 7 and producing a polypeptide of about 68,000 daltons having collagenase activity and distinguishable by the heterologous expression of the sequence of claim 3 from the endogenous production by *C. histolyticum* of multiple forms of collagenase by the essential absence of those forms of *C. histolyticum* collagenase having molecular weights of above about 70,000 daltons determined by the expression of the *C. histolyticum* genomic coding sequence, the polypeptide being sufficiently resistant to autocatalytic degradation that it is substantially stable on storage for about 2 days at about 25° C.

20. *E. coli* host cells transformed with the vector of claim 9 and producing a polypeptide of about 68,000 daltons having collagenase activity and distinguishable by the heterologous expression of the sequence of claim 3 from the endogenous production by *C. histolyticum* of multiple forms of collagenase by the essential absence of those forms of *C. histolyticum* collagenase having molecular weights of above about 70,000 daltons determined by the expression of the *C. histolyticum* genomic coding sequence, the polypeptide being sufficiently resistant to autocatalytic degradation that it is substantially stable on storage for about 2 days at about 25° C.

21. *E. coli* host cell transformed with the vector of claim 11 and producing:
    (i) a polypeptide of about 68,000 daltons having collagenase activity and distinguishable by the heterologous expression of the sequence of claim 3 from the endogenous production by *C. histolyticum* of multiple forms of collagenase by the essential absence of those forms of *C. histolyticum* collagenase having molecular weights of above about 70,000 daltons determined by the expression of the *C. histolyticum* genomic coding sequence, the polypeptide being sufficiently resistant to autocatalytic degradation that it is substantially stable on storage for about 2 days at about 25° C.; and (ii) a fusion polypeptide of molecular weight greater than 70,000 daltons displaying the antigenicity of *C. histolyticum* collagenase and containing at a least a portion of the amino acid sequence of *E. coli* galactosidase.

22. *E. coli* host cells transformed with the vector of claim 17 and producing two forms of collagenase:
    (i) a polypeptide of about 68,000 daltons having collagenase activity and distinguishable by the heterologous expression of the sequence of claim 3 from the endogenous production by *C. histolyticum* of multiple forms of collagenase by the essential absence of those forms of *C. histolyticum* collagenase having molecular weights of above about 70,000 daltons determined by the expression of the *C. histolyticum* genomic coding sequence, the polypeptide being sufficiently resistant to autocatalytic degradation that it is substantially stable on storage for about 2 days at about 25° C.; and
    (ii) polypeptides with molecular weights of from above 70,000 daltons to about 100,000 daltons and having collagenase activity.

23. The *E. coli* host cells of claim 22 wherein the polypeptide of about 68,000 daltons comprises greater than 50% by weight of the total polypeptides produced that have collagenase activity.

* * * * *